(12) United States Patent
Weston et al.

(10) Patent No.: US 7,341,725 B2
(45) Date of Patent: Mar. 11, 2008

(54) STRUCTURAL PROTEINS OF FISH PANCREATIC DISEASE VIRUS AND USES THEREOF

(75) Inventors: Jonathan Weston, Belfast (GB); Daniel Todd, Belfast (GB)

(73) Assignee: Intervet International B.V., Boxmeer (NL)

( * ) Notice: Subject to any disclaimer, the term of this patent is extended or adjusted under 35 U.S.C. 154(b) by 242 days.

(21) Appl. No.: 10/788,746

(22) Filed: Feb. 26, 2004

(65) Prior Publication Data

US 2004/0258707 A1    Dec. 23, 2004

Related U.S. Application Data

(62) Division of application No. 09/674,866, filed as application No. PCT/EP99/03244 on May 6, 1999, now Pat. No. 6,719,980.

(30) Foreign Application Priority Data

May 8, 1998 (EP) ................................. 98201461

(51) Int. Cl.
*A61K 39/12* (2006.01)

(52) U.S. Cl. ................................. 424/186.1; 424/218.1

(58) Field of Classification Search ...................... None
See application file for complete search history.

(56) References Cited

U.S. PATENT DOCUMENTS

| 5,914,260 | A | 6/1999 | McLoughlin et al. |
| 5,939,073 | A | 8/1999 | McLoughlin et al. |
| 6,719,980 | B1 | 4/2004 | Weston et al. |

FOREIGN PATENT DOCUMENTS

| EP | 0 712 926 | 5/1996 |
| NL | EP 0712926 A2 * | 5/1996 |

OTHER PUBLICATIONS

Houghton, G.: "Acquired Protection in Atlantic Salmon Salmo Salar Parr and Post-Smolts Against Pancreas Disease"; vol. 18 No. 2, Feb. 24, 1994, p. 109-118.

Schlesinger et al: Togaviridae: The Viruses and Their Replication. In B.M. Fields et al (ed.), Fields Virology, 3rd ed. Philadelphia, Lippencolt-Raven Publishers; 1996; 825-827.

Nelson, R., et al: "Isolation of a Toga-Like Virus from Farmed Atlantic Salmon Salmo Salar with Pancreas Disease", Diseases of Aquatic Organism, vol. 22, No. 1, May 4, 1995, p. 25-32.

* cited by examiner

*Primary Examiner*—Stacy B. Chen
(74) *Attorney, Agent, or Firm*—Aaron L. Schwartz; Mark W. Milstead

(57) ABSTRACT

The present invention relates to the structural proteins of the causative agent of Pancreatic Disease in fish, nucleotide sequences encoding said proteins, vaccines comprising said proteins or nucleotide sequences and diagnostic kits comprising said proteins or nucleotide sequences.

4 Claims, 2 Drawing Sheets pFastBac1 SPDV Constructs 1. p130 — NotI — Capsid — E3 — E2 — 6K — E1 — 3'NCR — NotI
3944nt 2. p98 — NotI ATG — E3 — E2 — 6K — E1 — 3'NCR — NotI
3098nt 3. PE2 (E3&E2) — NotI ATG — E3 — E2 — UGA NotI
1527nt 4. E2 — NotI ATG — E2 — UGA NotI
1314nt

FIGURE 1

```
TGC AGC AGG GTG CGG TAC TCT CTG GTC GCC AAC
 C   S   R   V   R   Y   S   L   V   A   N

ACG TTC AAC CCG AAC CCA CCA CCA TTG ACC GCA
 T   F   N   P   N   P   P   P   L   T   A
                                     E2 C-TERMINUS
CTG ACT GCA GCA CTG TGT TGC ATA CCA GGG GCT
 L   T   A   A   L   C   C   I   P   G   A
        | 6K PROTEIN
CGC GCG GAC CAA CCC TAC TTG GAC ATC ATT GCC  (27)
 R   A   D   Q   P   Y   L   D   I   I   A   (9)

TAC TTG TGG ACC AAC AGC AAA GTG GCC TTC GGG  (60)
 Y   L   W   T   N   S   K   V   A   F   G   (20)

CTA CAA TTT GCG GCG CCC GTG GCC TGT GTG CTC  (93)
 L   Q   F   A   A   P   V   A   C   V   L   (31)

ATC ATT ACA TAC GCC CTT AGG CAC TGC AGA TTG  (126)
 I   I   T   Y   A   L   R   H   C   R   L   (42)

TGC TGC AAG TCT TTT TTA GGG GTA AGA GGG TGG  (159)
 C   C   K   S   F   L   G   V   R   G   W   (53)

TCA GCC CTG CTG GTC ATC CTT GCG TAT GTA CAG  (192)
 S   A   L   L   V   I   L   A   Y   V   Q   (64)
        | E1 N-TERMINUS
AGC TGC AAG AGC TAC GAA CAC ACC GTG GTG GTC  (204)
 S   C   K   S   Y   E   H   T   V   V   V   (68)

CCA ATG GAT CCA AGA GCC CCG TCG TAC GAA GCA
 P   M   D   P   R   A   P   S   Y   E   A

GTG ATA AAC CGG AAT GGG TAT GAT CCA TTG AAG
 V   I   N   R   N   G   Y   D   P   L   K

CTG ACC ATC TCA GTG AAT TTC ACC GTC ATC TCA
 L   T   I   S   V   N   F   T   V   I   S

CCA ACT ACG GCT CTG GAA T      3'
 P   T   T   A   L   E
```

FIGURE 2

STRUCTURAL PROTEINS OF FISH PANCREATIC DISEASE VIRUS AND USES THEREOF

This application is a Division of U.S. application No.: 09/674,866, now U.S. Pat. No. 6,719,980, which is the National Stage of International Application PCT/EP99/03244, filed May 6, 1999, which claims priority to European patent application EP 98201461.5, filed May 8, 1998.

FIELD OF THE INVENTION

The present invention relates to the structural proteins of the causative agent of Pancreatic Disease in fish, nucleotide sequences encoding said proteins, vaccines comprising said proteins or nucleotide sequences and diagnostic kits comprising said proteins or nucleotide sequences.

BACKGROUND OF THE INVENTION

Pancreatic Disease (PD) is a serious disease that affects fish, in particular salmonid fish such as wild Atlantic salmon, rainbow trout and the like. The disease causes lesions in the pancreas, including loss of pancreatic exocrine tissue, and fibrosis, cardiac and skeletal muscle myopathies. Outbreaks of PD were first described in 1984 by Munro et al, in Helgoland Meeresuntersuchungen 37:571-586 (1984). PD typically affects the fish post-molts during the first year after they are transferred to sea sites and is reported to spread rapidly among farm fish held in sea cages. Clinical signs include lethargy with a tendency to congregate in cage corners and to fail to maintain a horizontal position, cessation of feeding (anorexia) and significant mortalities (Ferguson et al, J. Fish Disease 9:95-98, 1986). Murphy et al (in J. Fish Disease 15:401-408, 1992) confirmed these observations in a later study, in which it was found that cardiac and skeletal myopathy is exacerbated in fish suffering from PD.

An outbreak of PD in a fish farm can cause growth to be reduced and up to 10 percent of surviving fish may prove to be runt. On Irish fish farms PD causes significant mortality rates of 10 to 60 percent among the young fish during the first year after they are transferred to sea sites (McLoughlin, M., Fish Farmer page 19, March/April 1995). The estimated cost to the Irish industry in terms of loss of production is currently thought to be around £25 million per year. Consequently, there is a great need for a vaccine for the prevention and/or treatment of PD in fish.

EP-A-712926 describes the isolation of the causative agent of PD from tissues of PD affected fish arid the identification of the virus as a toga-like virus. To prevent PD infections in fish, the use of attenuated or inactivated PD for vaccination of the fish is accordingly suggested. A drawback in the production of inactivated vaccines from the PD virus described in EP-A-712926 is the slow growth of the virus, in particular on cell cultures, which makes the manufacturing of said vaccines a relatively inefficient process. A further drawback with the inactivated vaccines is the instability of the inactivated virus in the presence of other inactivated pathogens resulting in potency loss. Fish vaccines are generally produced as multivalent vaccines, and significant higher amounts of inactivated virus are required in the multivalent vaccine than would be necessary in a monovalent vaccine to compensate for the loss of potency.

DETAILED DESCRIPTION OF THE INVENTION

The present invention provides the means to produce alternative vaccines to prevent infection of fish with PD, in which the above mentioned difficulties are overcome. The present invention provides for the nucleotide sequence of the 3' part of the genomic RNA of a salmon PD virus (SPDV). This sequence of 5179 nucleotides is depicted in SEQ ID NO 1 and contains several open reading frames (ORF's): On the coding strand nucleotide 2 to 1186 codes for a non-structural protein, and another overlapping ORF starting from nucleotide 997 to 5076 codes for the structural proteins. This ORF was designated as p130. Other non-determined ORF's were found on the coding strand (3447 to 3767 and 4289 to 4612) and the non coding strand (1207 to 890, and 1232-837).

The ORF from nucleotide 2 to 1186 codes for the C-terminal part of a non-structural protein designated as NSP4; its deduced amino acid is depicted in SEQ ID NO 2.

ORF p130 comprises the nucleotide sequences that encode the structural proteins of the PD virus. The structural proteins of the PD virus consist of a basic capsid protein, three envelope proteins designated as E1, E2 and E3, and a protein designated as the 6K protein. The amino acid sequence of the whole protein encoded by the p130 ORF is depicted in SEQ ID NO 3. After processing, the p130 protein is spliced into the capsid protein (aa 76-375 of p130), E3 (aa 358-428 of p130), E2 (aa429-866 of p130), 6K (aa 867-898 of p130), and E1 (aa 899-1359 of p130).

The nucleotide sequence encoding the capsid protein of the PD virus is located at nucleotide 1222 to 2067 of SEQ ID NO 1. The corresponding amino acid sequence (total 282 amino acids) is depicted in SEQ ID NO 4.

The nucleotide sequence encoding the envelope proteins E3, E2 and E1 are located at nucleotide 2068-2280, 2281-3594 and 3691-5076 respectively, of the nucleotide sequence depicted in SEQ ID NO 1. The corresponding amino acid sequences of the E3, E2 and E1 proteins are depicted in SEQ ID No's 5, 6 and 8 respectively.

The nucleotide sequence encoding the 6K protein is located at nucleotide 3595 to 3690 of the nucleotide sequence depicted in SEQ ID NO 1, and the corresponding amino acid sequence of the 6K protein is depicted in SEQ ID NO 7. Further sequence analysis of the viral RNA extracted from PD infected pancreas tissue revealed the existence of a longer variant of the 6K protein having 68 amino acids in length compared to the 6K protein of 32 amino acids depicted in SEQ ID NO 7. The nucleotide sequence (SEQ ID NO 14) encoding the longer variant of 6K protein is 204 nucleotides in length compared to the 96 nucleotides of the nucleotide sequence encoding the truncated 6K protein. The nucleotide sequence encoding the long variant of 6K protein and the deduced amino acid sequence thereof are shown in FIG. 2 and SEQ ID NO 14 and SEQ ID NO 15 respectively.

The cloning and characterisation of the nucleotide sequences of the present invention provides for the production of the structural proteins of the PD virus using standard recombinant DNA technology (Sambrooke et al., Molecular Cloning: a Laboratory Manual, Cold Spring Harbor Laboratory Press, Cold Spring Harbor, 1989). Cloning techniques and subsequent protein expression using in vitro expression systems are well known in the art. In this way, recombinant structural PDV proteins can be obtained, that are substantially free from other PDV proteins. These isolated structural proteins can be used to manufacture subunit vaccines to protect against infection of PD in fish. Said subunit vaccines may be used as marker vaccine in fish to distinguish vaccination from field infections with PD. Alternatively the nucleotide sequences encoding the structural proteins of the PD virus can be used to manufacture DNA vaccines or vector vaccines to protect against infection of fish with PD.

The nucleotide sequences and recombinant PD proteins can furthermore be used for diagnostic purposes, for instance to detect the presence of PD virus in the field or anti-PD antibodies in fish. Additionally, the recombinant PD proteins of the present invention can be used to produce PD specific antibodies. These antibodies can also be used for diagnostic purposes such as the detection of PD virus in fish or in the field.

Thus, in a first aspect the invention provides for a nucleic acid comprising the nucleotide sequence depicted in SEQ ID NO 1 encoding the structural proteins and part of NSP4 of the PD virus, fragments of said nucleotide sequence and a nucleic acid comprising the nucleotide sequence depicted in SEQ ID NO 14. Preferred fragments of the nucleotide sequences according to the invention are nucleotide fragments 1222-5076 (also referred to as p130 encoding the capsid, E3, E2, 6K and E1 proteins), 2068-5076 (also referred to as p98 encoding the E3, E2, 6K and E1 proteins), 2068-3594 (also referred to as pE2 encoding E3 and E2 proteins), 1222-15 2067 (capsid), 2068-2280 (E3), 2281-3594 (E2), 3595-3690 (6K), and 3691-5076 (E1). For the purpose of this invention the nucleotide sequences according to the present invention also encompass the nucleotide sequence depicted in SEQ ID NO 1 and fragment sequences thereof (such as the p 130 and p98 fragments) which at least comprise a nucleotide sequence encoding for a 6K protein, wherein the nucleotide sequence depicted by nucleotide 3595-3690 of SEQ ID NO 1 has been substituted with the nucleotide sequence depicted in SEQ ID NO 14. Also within the scope of this invention are nucleic acids comprising tandem arrays of the nucleotide sequence comprising the sequence depicted in SEQ ID NO 1 or SEQ ID NO 14 or fragments thereof. Nucleotide sequences that are complementary to the sequence depicted in SEQ ID NO 1, SEQ ID NO 14, or parts thereof are also within the scope of the invention, as well as nucleotide sequences that hybridise with the sequence depicted in SEQ ID NO 1 or SEQ ID NO 14. The hybridisation conditions for this purpose are stringent, preferably highly stringent. According to the present invention the term "stringent" means washing conditions of 1×SSC, 0.1% SDS at a temperature of 65° C.; highly stringent conditions refer to a reduction in SSC towards 0.3×SSC. Nucleotide sequences that hybridise with the sequence shown in SEQ ID NO 1 or SEQ ID NO 14 are understood to be nucleotide sequences that have a sequence homology of at least 70%, preferably 80%, and more preferably 90% with the corresponding matching part of the sequence depicted in SEQ ID NO 1 or SEQ ID NO 14. According to the present invention the sequence homology is determined by comparing the nucleotide sequence with the corresponding part of the sequence depicted in SEQ ID NO 1 or SEQ ID NO 14. The sequence homology between a to nucleotide and the sequence in SEQ ID NO 1 or SEQ ID NO 14 can be determined via common sequence analysis program such as BLASTN and the like. The optimal match area is automatically determined by these programs. Homologous sequences can easily be isolated from closely related PD virus strains with the sequence depicted in SEQ ID NO 1 or SEQ ID NO 14, or fragments of these sequences, using routine cloning and hybridisation techniques. Sleeping Disease (SD) virus is closely related to PD virus and the nucleic acid sequences encoding the structural capsid, E3, E2, E 1 and 6K proteins of SD virus have the necessary sequence homology with the nucleic acid sequences depicted in SEQ ID NO 1 and 14. Thus, these SD nucleic acid sequences are also within the present invention. The nucleotide sequences of the invention can be used in the preparation of a DNA vaccine to vaccinate fish against PD infection. DNA vaccination refers to the induction of an immune response to one or more antigens that are expressed in vivo from a gene inserted in a DNA plasmid which has been inoculated directly into the vaccinated fish. Thus, in a second aspect of the invention there is provided for a DNA vaccine comprising a pharmaceutically acceptable carrier and a DNA plasmid in which a nucleotide sequence encoding one or more PDV structural proteins is operably linked to a transcriptional regulatory sequence.

Preferably the nucleotide sequence to be used in said DNA plasmid is a nucleotide sequence comprising the nucleotide sequence depicted in SEQ ID NO 1 or a nucleotide sequence comprising the nucleotide sequence depicted in SEQ ID NO 14 or fragments of said nucleotide sequences. Preferred fragments of the nucleotide sequence depicted in SEQ ID NO 1 or 14 are nucleotide fragments 1222-5076, 2068-5076, 2068-3594, 1222-2067, 2068-2280, 2281-3594, 3595-3690 3691-5076 of the sequence depicted in SEQ ID NO 1, and combinations thereof such as for example fragment 1222-2067 with fragment 2281-3594. Also suitable for use in said DNA plasmid are nucleotide sequences that are complementary to the sequence of SEQ ID NO 1 or SEQ ID NO 14 or nucleotide sequences of which the sequence homology with the sequence depicted in SEQ ID NO 1 or SEQ ID NO 14 is at least 70%, preferably 80%, more preferably 90%. The sequence homology between the nucleotide sequences that are suitable for use in the DNA plasmid is determined as described earlier.

DNA plasmids that are suitable for use in a DNA vaccine according to the invention are conventional cloning or expression plasmids for bacterial, eukaryotic and yeast host cells, many of which are commercially available. Well known examples of such plasmids are pBR322 and pcDNA3 (Invitrogen). The DNA plasmids according to the invention should be able to induce protein expression of the nucleotide sequences. The DNA plasmid can comprise one or more nucleotide sequences according to the invention. In addition, the DNA plasmid can comprise other nucleotide sequences such as the immune-stimulating oligonucleotides having unmethylated CpG dinucleotides, or nucleotide sequences that code for other antigenic proteins or adjuvating cytokines.

Transcriptional regulatory sequences that are suitable for use in a DNA plasmid according to the invention comprise promoters such as the (human) cytomegalovirus immediate early promoter (Seed, B. et al., Nature 329, 840-842, 1987; Fynan, E. F. et al., PNAS 90, 11478-11482,1993; Ulmer, J. B. et al., Science 259, 1745-1748, 1993), Rous sarcoma virus LTR (RSV, Gorman, C. M. et al., PNAS 79, 6777-6781, 1982; Fynan et al., supra; Ulmer et al., supra), the-MPSV LTR (Stacey et al., J. Virology 50, 725-732, 1984), SV40 immediate early promoter (Sprague J. et al., J. Virology 45, 773, 1983), the metallothionein promoter (Brinster, R. L. et al., Nature 296, 39-42, 1982), the major late promoter of Ad2, the β-actin promoter (Tang et al., Nature 356, 152-154, 1992). The regulatory sequences may also include terminator and polyadenylation sequences. Amongst the sequences that can be used are the well known bovine growth hormone polyadenylation sequence, the SV40 polyadenylation sequence, the human cytomegalovirus (hCMV) terminator and polyadenylation sequences.

The DNA plasmid comprising a nucleotide sequence according to the present invention operably linked to a transcriptional regulatory sequence for use in the vaccine according to the invention can be naked or can be packaged in a delivery system. Suitable delivery systems are lipid vesicles, Iscoms, dendromers, niosomes, polysaccharide matrices, and the like. Also very suitable as delivery system are attenuated live bacteria such as Salmonella.

The nucleotide sequences according to the invention can additionally be used in the production of a vector vaccine to vaccinate fish against PD. A vector vaccine is understood to be a vaccine in which a live, attenuated bacteria or virus has been modified so that it contains one or more heterologous nucleotide sequences inserted is into its genetic material. These so called vector bacteria or viruses are capable of coexpressing the heterologous proteins encoded by the inserted nucleotides. Thus in a third aspect the invention provides for a vector vaccine comprising a live attenuated bacteria or virus which have been modified to comprise in their genetic material one or more of the nucleotide sequences of the present invention. Very suitable for use as a vaccine vector are for example vaccinia virus or Semliki forest virus The nucleotide sequences according to the invention can also be used for the recombinant production of structural PD proteins, substantially free from other PD proteins. Thus in a fourth aspect the invention provides for the structural proteins from PD virus. More specifically the invention provides for a PD capsid protein, the PD envelope proteins E1, E2, and E3, and the 6K protein. In particular there is provided for a capsid protein having the amino acid sequence depicted in SEQ ID NO 4 or a derivative thereof, an E3 protein having the amino acid sequence depicted in SEQ ID NO 5 or a derivative thereof, an E2 protein having the amino acid sequence depicted in SEQ ID NO 6 or a derivative thereof, an E1 protein having the amino acid sequence depicted in SEQ ID NO 8 or a derivative thereof, and a 6K protein having the amino acid sequence depicted in SEQ ID NO 7, SEQ ID NO 15 or a derivative thereof.

Derivative proteins are understood to be proteins which have alterations in the amino acid sequence(s) of the present invention which do not affect the antigenic and/or immunogenic characteristics of these proteins, that is these derivative proteins are still capable of inducing the production of antibodies that recognise and (cross)-react with the PD virus and/or inducing an immune response in fish that protects against PD infection. Antigenic characteristics are understood to be the ability to induce production of antibodies that recognise and (cross)-react with the PD virus. Immunogenic characteristics are understood to be the ability to induce an immune response in fish that protects against infection with PD. The alterations that can occur in a sequence according to the present invention could for instance result from conservative amino acid substitutions, deletions, insertions, inversions or additions of (an) amino acid(s) in the overall sequence. Amino acid substitutions that are expected not to alter the immunological properties have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science, 1985, vol. 227, 1435-1441) and determining the functional similarity between proteins and peptides having sequence homology. The derivative proteins according to the invention are still capable to induce the production of antibodies that recognise and (cross)-react with the PD virus and/or to induce an immune response in the fish that protects against PD infection. The capsid, E1, E2, E3, and 6K proteins derived from Sleeping Disease (SD) virus are such derivative proteins according to the invention. These proteins have an amino acid sequence that is identical or almost identical to those of the PD virus as depicted in SEQ ID NO 4 to 8 or 15. These proteins are capable to raise antibodies that recognize and cross-react with PD virus as well as SD virus. Other derivatives are protein fragments that are still capable to induce the production of antibodies that recognise and (cross)-react with the PD virus and/or to induce an immune response in the fish. The proteins according to the invention can be prepared via standard recombinant protein expression techniques. For this purpose a nucleotide sequence encoding one or more of the proteins according to the invention or a multimere of said protein is inserted into an expression vector. Preferably the nucleotide sequence is a nucleotide sequence comprising the nucleotide sequence depicted in SEQ ID NO 1 or SEQ ID NO 14 or one or more fragments of these sequences. Preferred fragments of the nucleotide sequences according to the invention are nucleotide fragments 1222-5076, 2068-5076, 2068-3594, 1222-2067, 2068-2280, 2281-3594, 3595-3690 3691-5076 of the sequence depicted in SEQ ID NO 1, and combinations thereof such as, for example, fragment 1222-2067 with fragment 2281-3594. Further preferred fragments according to the invention are fragments of the nucleotide sequence depicted in SEQ ID NO 15 such as, for example, the nucleotide sequence depicted by nucleotides 3595-3690 of SEQ ID NO 1. Also suitable are nucleotide sequences that are complementary to the sequence of SEQ ID NO 1 or SEQ ID NO 14 or nucleotide sequences of which the sequence homology with the sequence depicted in SEQ ID NO 1 or SEQ ID NO 14 is at least 70%, preferably 80%, and more preferably 90%. The sequence homology between the nucleotide sequences that are suitable for use in the DNA plasmid is determined as described earlier.

Suitable expression vectors are, amongst others, plasmids, cosmids, viruses and YAC's (Yeast Artificial Chromosomes) which comprise the necessary control regions for replication and expression. The expression vector can be brought to expression in a host cell. Suitable host cells are, for instance, bacteria, yeast cells and mammalian cells. Such expression techniques are well known in the art (Sambrooke et al., Molecular Cloning: a Laboratory Manual, Cold Spring Harbor Laboratory Press, Cold Spring Harbor, 1989).The expressed proteins can be isolated and purified from the medium. Expression of the whole p130 ORF (nucleotide fragment 997 to 5076 of SEQ ID NO 1) might lead to the forming of virus-like particles due to the spontaneous assemblance of the structural proteins. The invention furthermore provides for a vaccine comprising one or more of the structural PD proteins and a pharmaceutically acceptable carrier. More specifically, a vaccine according to the invention comprises a capsid protein having an amino acid sequence depicted in SEQ ID NO 4 or a derivative thereof, an E3 protein having an amino acid sequence depicted in SEQ ID NO 5 or a derivative thereof, an E2 protein having an amino acid sequence depicted in SEQ ID NO 6 or a derivative thereof, an E1 protein having an amino acid sequence depicted in SEQ ID NO 8 or a derivative thereof, a 6K protein having an amino acid sequence depicted in SEQ ID NO 7 or SEQ ID NO 15 or a derivative thereof, or a mixture comprising two or more of the to proteins according to the invention. Preferably the vaccine according to the invention comprises the E2 protein, and optionally the capsid protein. Also preferred is a vaccine comprising all structural proteins of PD; these proteins can spontaneously form virus-like particles, thus providing a vaccine that closely resembles that of the whole pathogen. Vaccines according to the invention are suitable for use as a marker vaccine to distinguish between vaccination and infection by PD in the field. A preferred vaccine according to the invention is a marker vaccine comprising a 6K protein having the amino acid sequence depicted in SEQ ID NO 7.

A vaccine according to the invention can be prepared according to techniques well known to the skilled practitioner. General techniques for the preparation of DNA vaccines have been widely described, for example in EP patent 0 773 295 and U.S. Pat. No. 5,580,859.

Vaccines according to the invention comprise an effective amount of the afore-mentioned DNA plasmids, vector bacteria or virus, or proteins and a pharmaceutically acceptable carrier. The term "effective" as used herein is defined as the amount sufficient to induce an immune response in the target fish. The amount of plasmid, vector or protein will depend on the type of plasmid or vector, the route of administration, the time of administration, the species of the fish as well as age, general health and diet.

In general, a dosage of 0.01 to 1000 μg protein per kg body weight, preferably 0.5 to 500, more preferably 0.1 to 100 μg protein can be used. With respect to the DNA vaccines, generally a minimum dosage of 10 pg. up to dosages of 1000 μg of plasmid have been described to be sufficient for a suitable expression of the antigens in vivo.

Pharmaceutically acceptable carriers that are suitable for use in a vaccine according to the invention are sterile water, saline, aqueous buffers such as PBS and the like. In addition, a vaccine according to the invention may comprise other additives such as adjuvants, stabilisers, anti-oxidants and others.

Suitable adjuvants include, amongst others, aluminium hydroxide, aluminium phosphate, amphigen, tocophenols, monophosphenyl lipid A, muramyl dipeptide, oil emulsions, glucans, carbomers, block-copolymers, cytokines and saponins such as Quil A. The amount of adjuvant added depends on the nature of the adjuvant itself.

Suitable stabilisers for use in a vaccine according to the invention are for example carbohydrates including sorbitol, mannitol, starch, sucrose, dextrin, and glucose, proteins such as albumin or casein, and buffers like alkaline phosphates.

The vaccines according to the invention are administered to the fish via injection, spray, immersion or peroral. The administration protocol can be optimised in accordance with standard vaccination practice.

The nucleotide sequences and the proteins according to the invention are also suitable for use in diagnostics. The nucleotide sequences or fragments thereof can be used to detect the presence of PD virus in the fish. A primer spanning the C-terminal part of E2/6K/N-terminal part of E1 (see FIG. 2) was used in RT-PCR to succesfully detect the presence of PD virus in a clinical specimen of a PD outbreak. The proteins can be used to detect the presence of antibodies in the fish.

The proteins according to the invention can additionally be used for the production of antibodies, using the general techniques available to the practitioner in the field. Preferably the proteins are used to produce specific monoclonal antibodies. The obtained antibodies may be utilised in diagnostics, to detect PD virus in the field, or in the fish.

Thus, in another aspect, the present invention provides for a diagnostic kit comprising one or more nucleotide sequences according to the invention, or one or more structural proteins according to the invention, or antibodies obtained with said proteins. Antibodies according to the invention can be prepared according to standard techniques. Procedures for immunising animals, e.g. mice with proteins and selection of hybridomas producing immunogen specific monoclonal antibodies are well known in the art (see for example Coligan et al. (eds), Current protocols in Immunology, 1992; Kohler and Milstein, Nature 256:495-497, 1975; Steenbakkers et al., Mol. Biol. Rep. 19:125-134, 1994).

The following examples are to illustrate the invention and should not be interpreted to limit the invention in any way.

BRIEF DESCRIPTION OF THE FIGURES

FIG. 1: structural organisation of the various cloned nucleotide sequences coding for the PD structural proteins.

FIG. 2: Nucleotide sequenec of C-terminus of E2 gene (nucleotides 3490-3594 of SEQ ID NO.:1; encoding amino acids 404-438 of SEQ ID NO.:6)/"long"6K gene (nucleotides 1-204 of SEQ ID NO.:14; encoding amino acids 1-68 of SEQ ID NO.: 15)/N-terminus of E1gene (nucleotides 3691-3829 of SEQ ID NO.:1: encoding amino acids 1-46 of SEQ ID NO.:8). The putative cleavage sites between the E2/6K protein and 6K/E1 protein are represented by the vertical line (|) The nucleotide sequence encoding the "long"6K protein is 204 nucleotides long and encodes a protein of 68 amino acids. The numbering between brackets on the right of the sequence refers to the nucleotide and amino acid residues of the 6K gene or protein respectively. At nucleotide position 44 of the nucicotide sequence encoding the 6K gene the G-residue can be replaced with an A residue, resulting in a 6K protein with an N residue at amino acid position 15 of the amino acid sequence depicted in the figure.

EXAMPLES

Cells and Virus

Isolation and cultivation of a salmon PD virus (SPDV) strain was carried out in general as described in EP-A-712926. The F93125 isolate of SPDV was grown in Chinook salmon embryo (CHSE-214) cells as previously described (R. T. Nelson et al. (1995) Isolation of toga-like virus from farmed Atlantic salmon *Salmo salar* with pancreas disease. Diseases of Aquatic Organisms 22, pp. 25-32). For virus purification purposes, monolayer cultures of CHSE-214 grown to ~80% confluence in 75 $cm^2$ flasks were infected with 1 ml virus to give a multiplicity of infection of ~1. After 1 hr.adsorption an additional 14 ml supplemented Eagle's minimal essential medium (MEM) was introduced to each flask. The virus infected flasks were incubated at 15° C. for 7 or 8 days, when virus-induced cytopathic effect was evident, and the supernatant was collected.

Virus Purification

The supernatant (typically 500 ml from virus-infected cells was clarified at 3000 g for 20 min. Polyethyleneglycol (PEG) and NaCl were added to give final concentrations of 6% and 2.2% respectively. Following overnight incubation at 4° C. the PEG precipitate was collected by centrifugation for 2 h at 3000 g. The resultant pellet was resuspended in PBS (1-2 ml) and, after clarification at 1000 g for 5 minutes, the crude virus suspension was fractionated by equilibrium density centrifugation using 11 ml gradients (20-60% w/w in PBS) of sucrose. After centrifugation for 18 hr at 75000 g at 4° C., 1 ml fractions were collected from the bottom of the gradient. Fractions containing virus were identified by immunoblotting using an PD-specific mouse monoclonal antibody (Welsh et al., submitted 1999).

Production of PD Virus cDNA Clones

Viral RNA was extracted from gradient-purified PD virus and virus-infected cells using RNA isolator (Genosys) and stored as ethanol precipitates. A cDNA library was made by random priming with RNA extracted from gradient-purified virus. This library consisted of clones containing inserts (250-500 bp) in the vector pUC18 (Sureclone ligation Kit, Pharmacia). Clones were selected randomly from the library and following sequencing and analysis using the BLAST program (University of Wisconsin, Genetics Computer Group) were mapped to the alphavirus genome. The sequences of three clones, N11, N38 and N50, were used to design oligonucleotide primers that were used in reverse transcription-polymerase chain reaction (RT-PCR) to amplify 3 overlapping fragments encompassing the 5.2 kb region at the 3'terminus of the PD genome. The incorporation of Not I sites into the primers facilitated the restriction ligation of two of these fragments into the Not I site of vector pBluescript (Stratagene). PCR was carried out using Expand Long Template PCR System (Boehringer Mannheim) at 94° C. for 30 s 60° C. for 30 s, 68° C. for 2 min. Another clone was produced using 3'RACE (M. A. Frohmann et al., 1998; Rapid production of full-length cDNA's from rare transcripts using a single gene-specific oligonucleotide primer. Proc. Natl. Acad. Sci.USA. 85, pp. 8998-9002). The reaction was performed using a 5'/3' RACE kit (Boehringer Mannheim) with some modifications. Thus, RNA from gradient-purified virus was independently subjected to first-strand synthesis and the resultant cDNA's were amplified by PCR at 94° C. for 30 s, 60° C. for 30 s, 68° C. for I min.

Sequencing of PD Virus cDNA Clones

Cycle sequencing was performed using the ABI PRISM dye terminator ready reaction kit on purified plasmid DNA following the manufacturers protocol (Perkin Elmer Cetus). Electropherograms were interpreted using the Sequence Navigator software (Perkin Elmer Cetus). The complete nucleotide sequence of the 3'terminal 5.2 kb region of the PD virus RNA is presented in SEQ ID NO1.

An RT-PCR and sequence analysis using primers flanking the C-terminus of E2 and the N-terminus of E1 for viral RNA extracted directly from PD infected pancreas tissue revealed a longer 6K-encoding nucleotide sequence than the one depicted by nucleotides 3595-3690 of SEQ ID NO 1. The nucleic acid encoding the full-length 6K protein as well as the deduced amino acid sequence are shown in FIG. 2.

SPDV pFastBac1 and pcDNA3.1 (+) Constructs

Using standard cloning techniques (Sambrooke et al., Molecular Cloning: a Laboratory Manual, Cold Spring Harbor Laboratory Press, Cold Spring Harbor, 1989) four clones representing the SPDV structural region have been created in the vector pFastBac1 (Gibco BRL) for expression in the baculovirus system. These clones have also been created in the expression vector pcDNA3.1 (Invitrogen) for monoclonal antibody characterisation and use as a DNA vaccine. Details of how these clones have been produced are as follows:

Clone 1.

p130 encodes the complete structural gene region from the 1st ATG of the capsid protein to the poly(A) tract (3944nt). cDNA was produced from viral RNA by RT-PCR using the following primers:

```
5' forward primer (5'130Not1):
5'-TGC ATG CGG CCG CAT GTT       (SEQ ID NO 9)
TCC CAT GCA ATT CAC CAA C-3'

3' inverse primer (3'130Not1) (sequence 5' to 3'):
5'-TGC ATG CGG CCG CTT GTA       (SEQ ID NO 10)
TTG AAA ATT TTA AAA CCA A-3'
```

These primers contain a 5 nucleotide stretch (ensures restriction enzyme recognition) followed by a Not1 site then the appropriate SPDV sequence (highlighted in the attached sequence, from 1222 to 1245 for 5'130Not1 and from 5143 to 5166 for 3'130Not1). The 3944nt cDNA product was cloned into the Not1 site in both pFastBac1 and pcDNA3.1.

Clone 2.

p98 encodes for E3, E2, 6K and E1 to the poly(A) tract (3098nt). cDNA was produced from viral RNA by RT-PCR using the following primers:

```
5' forward primer (5'E3Not1):
5'-TGC ATG CGG CCG CAT GAC ACG   (SEQ ID NO 11)
CGC TCC GGC CCT CCT G-3'

3' inverse primer (3'130Not1):
5'-TGC ATG CGG CCG CTT GTA TTG   (SEQ ID NO 10)
AAA ATT TTA AAA CCA A-3'
```

The primer 5'E3Not1 contains a 5 nucleotide stretch (ensures restriction enzyme recognition) followed by a Not1 site, an ATG (artificial start codon) then the appropriate SPDV sequence (from 2067 to 2088) The primer 3'130Not1 is as described above in Clone1. The 3098nt cDNA product was cloned into the Not1 site in both pFastBac1 and pcDNA3.1.

Clone 3.

pE2 encoding the E3 and E2 glycoproteins (1527nt). cDNA was produced from viral RNA by RT-PCR using the following primers:

```
5' forward primer (5'E3Not1):
5'-TGC ATG CGG CCG CAT GAC ACG   (SEQ ID NO 11)
CGC TCC GGC CCT CCT G-3'

3' inverse primer (3'E2Not1):
5'-TGC ATG CGG CCG CTC ACG CGC   (SEQ ID NO 12)
GAG CCC CTG GTA TGC AAC A-3'
```

The primer 5'E3Not1 is as described above in Clone2. The primer 3'E2Not1 contains a 5 nucleotide stretch (ensures restriction enzyme recognition) followed by a Not1 site, a TGA (artificial stop codon) then the appropriate SPDV sequence (highlighted in the attached sequence, from 3571 to 3594). The 1527nt cDNA product was cloned into the Not1 site in both pFastBac1 and pcDNA3.1.

Clone 4.

E2 encoding the E2 glycoprotein (1314nt). cDNA was produced from viral RNA by RT-PCR using the following primers:

```
5' forward primer (5'E2Not1):
5'-TGC ATG CGG CCG CAT GGC TGT   (SEQ ID NO 13)
GTC TAC GTC GCC TGC C-3'

3' inverse primer (3'E2Not1):
5'-TGC ATG CGG CCG CTC ACG CGC   (SEQ ID NO 12)
GAG CCC CTG GTA TGC AAC A-3'.
```

The primer 5'E2Not1 contains a 5 nucleotide stretch (ensures restriction enzyme recognition) followed by a Not1 site, an ATG (artificial start codon) then the appropriate SPDV sequence (from 2281 to 2301). The primer 3'E2Not1 is as described above in Clone 3. The 1314nt cDNA product was cloned into the Not1 site in both pFastBac1 and pcDNA3.1.

Insect cells (SF-9)were infected with the four recombinant baculovirus constructs. Using monoclonals that were raised against whole-inactivated PD virus, an IFT staining was performed on these recombinant baculovirus infected SF-9 cells. All produced proteins reacted positively with the monoclonals, indicating that the recombinant proteins possess the wild-type epitopes.

Challenge Experiments

The proteins produced by all four constructs were collected using Triton extraction. The proteins were BPL inactivated to prevent possible spread of surviving recombinant baculoviruses in the environment. The proteins were formulated into water-in-oil based vaccine formulations and injected in a 0.2 ml vaccine volume ELISA analysis using anti-PD-E2 monoclonals (2D9 capture and 7A2) showed that the amount of reactive epitopes per dose recombinant vaccine was comparable or even higher than the amount of epitopes found in a dose of the conventional inactivated PD virus vaccine. A standardized challenge experiment performed at 8 weeks post-vaccination in Atlantic salmon fish showed that protection against challenge with salmon PD virus could be obtained with these recombinant sub-unit vaccines. In the experiment, 20 lesions in pancreas, skeletal muscle and heart muscle were scored in ordinary way. Significant levels were calculated from Kruskal-Wallis one-way analysis of variance (non-parametric test). The vaccine formulation comprising the E2 or E2-E3 proteins gave similar levels of protection as obtained by the inactivated PD virus vaccine, while vaccines containing the recombinant proteins resulting from the p130 and p98 constructs respectively were less protective then the inactivated PD virus vaccine.

Production of Antibodies.

DNA vaccination with proteins obtained from expression of the p130 nucleotide construct was carried out in mice to test for the antigenic properties of the recombinant proteins. After two intramuscular inoculations with p130-pcDNA3.1 recombinant expression plasmids (see clone 1), the sera of mice showed an antibody reaction with in vitro produced PD virus.

The invention claimed is:

1. A recombinant protein of Fish Pancreatic Disease virus, wherein said recombinant protein is an E2 protein.

2. The recombinant protein of claim 1, wherein the recombinant protein comprises SEQ ID NO:6.

3. A composition comprising the recombinant protein of claim 1 and a phannaceutically acceptable carrier.

4. A diagnostic kit, comprising the recombinant protein of claim 1.

* * * * *

SEQUENCE LISTING

```
<160> NUMBER OF SEQ ID NOS: 15

<210> SEQ ID NO 1
<211> LENGTH: 5179
<212> TYPE: DNA
<213> ORGANISM: Salmon pancreatic disease virus

<400> SEQUENCE: 1
gactatggac tcagcggcaa tgaacgtgga ggcttttaaa agtttcgcct gtaaggacac      60
cgacctgtgg actgagttcg cggaaaaacc agtaaggttg tcgcccggcc aaatcgaaga     120
gtatgtcttt catctacaag gggccaaggc caatgtgatg cacagcagag tcgaagccgt     180
atgccctgac ctctcggagg tggctatgga caggttcaca ctagacatga aacgcgacgt     240
caaagtgacg ccaggcacga agcacgtaga ggagagacct aaagtccaag agattcaagc     300
ggccgacccc atggccaccg cgtacttgtg cgccatccat agagagctag tccgaaggct     360
gaaggccgtc ctgaaaccgt ctatacacgt gttgttcgat atgagctccg aggattttga     420
tgctatcgtg ggccatggga tgaagttggg tgacaaggtg ctggaaacgg acatctcctc     480
attcgacaag agccaggacc aagccatggc ggttacagcg ctgatgctgc tgagggactt     540
gggagtagaa gaagacctcc tgaccctaat tgaggcgtct ttcggcgaca tcacttctgc     600
ccacctgccc acaggcacca gatttcagtt tggatcgatg atgaagtctg gactttttct     660
gacgctgttc gtgaacacgc tgcttaacat caccatagct gcccgagttt tacgggagca     720
gctggctgat accaggtgtg ccgcgtttat cggtgacgac aacgtaatca ccggagtagt     780
gtctgacgac atgatggtgg ccaggtgcgc atcctggctg aacatggagg tgaagatcat     840 ggacatgaa attggcaaca tgagtcctta tttttgtggc ggcttcctgt tactcgacac     900
ggtaacaggc actgtaagcc gagtgtcgga ccctgtaaaa cgcctgatga agatgggaaa     960
accggccctg aacgatccag aaacggacgt ggacagatgc cgcgcactgc gcgaagaagt    1020
ggaaagctgg tacagagtgg ggattcagtg gccactgcag gtggctgccg ccacacgcta    1080
tggcgtgaac cacctgccgc tggccacaat ggcgatggcc acgctcgccc aggacttgag    1140
atcgtacctg ggcgcgcgag gggagtacgt atccctctac gtctaacctt aatattttct    1200
gcatcatact tccaaacaat catgtttccc atgcaattca ccaactcagc ctatcgccag    1260
atggagccca tgtttgcacc gggttcccga ggacaagtac agccgtaccg gccgcgcact    1320
aagcgccgcc aggagccgca agtcggcaac gccgccatta ctgccctcgc gaaccagatg    1380
```

-continued

```
agtgcgctcc agttgcaggt agctggactt gccggccagg caagggtgga ccgccgtggg      1440
ccaagacgtg ttcagaagaa caagcagaag aagaagaact cttccaacgg agaaaaaccc      1500
aaagagaaga agaagaagca aaaacaacag gagaagaagg gaagcggtgg cgaaaaagtc      1560
aagaagacta ggaaccgacc cgggaaggag gtaaggatct ccgtaaagtg tgcccgacag      1620
agcaccttcc ccgtgtacca cgaaggtgct atatccggct acgctgtgct gattggatct      1680
cgcgtattca agccggcaca cgtgaagggt aagatcgacc ccctgaact ggcagacatc       1740 aagttccagg tcgccgagga catggacctc gaagcagctg cgtacccgaa gagcatgcga      1800
gaccaagcgg ctgaaccagc gaccatgatg gacagagtgt acaactggga gtatggcact      1860
atcagagtgg aggataatgt cataatcgac gcaagcggta ggggcaagcc gggtgacagt      1920
ggcagggcca tcaccgacaa ctcgggaaag gttgttggta ttgtcctcgg aggaggaccc      1980
gatggcaggc gcacacgcct ctccgtgata ggtttcgaca agaagatgaa ggctagggag      2040
atcgcctaca gtgatgccat accttggaca cgcgctccgg ccctcctgct gctgcctatg      2100
gttattgtct gcacctacaa ttccaacacc ttcgattgct ccaaaccgtc ctgccaggac      2160
tgctgcatta ctgctgaacc agagaaggcc atgaccatgc tgaaggacaa tctgaacgac      2220
ccgaactact gggacctact cattgctgtc accacctgtg gctccgcccg gagaaagagg      2280
gctgtgtcta cgtcgcctgc cgccttttac gacacacaga tcctcgccgc ccacgcagct      2340
gcctccccat acagggcgta ctgccccgat tgtgacggaa cagcgtgtat ctcgccgata      2400
gccatcgacg aggtggtgag cagtggcagc gaccacgtcc tccgcatgcg ggttggttct      2460
caatcgggag tgaccgctaa gggtggtgcg gcgggtgaga cctctctgcg atacctggga      2520
agggacggga aggttcacgc cgcagacaac acgcgactcg tggtgcgcac gactgcaaag      2580
tgcgacgtgc tgcaggccac tggccactac atcctggcca actgcccagt ggggcagagc      2640
ctaaccgttg cggccacact ggatggcacc cggcatcaat gcaccacggt tttcgaacac      2700
caagtaacgg agaagttcac cagagaacgc agcaagggcc accatctgtc cgacatgacc      2760
aagaaatgca ccagatttc cactacacca aaaaagtccg ccctctacct cgttgatgtg       2820
tatgacgctc tgccgatttc tgtagagatt agcaccgtcg taacatgcag cgacagccag      2880
tgcacagtga gggtgccacc tggtaccaca gtgaaattcg acaagaaatg caagagcgct      2940
gactcggcaa ccgtcacttt caccagcgac tcccagacgt ttacgtgtga ggagccagtc      3000
ctaacggctg ccagtatcac ccagggcaag ccacacctca gatcggcaat gttgcctagc      3060
ggaggcaagg aagtgaaagc aaggatcccg ttcccgttcc cgccggaaac cgcaacttgc      3120
agagtgagtg tagcccccact gccgtcgatc acctacgagg aaagcgatgt cctgctagcc      3180
ggtaccgcaa ataccctgt gctgctaacc acacggaacc ttggtttcca tagcaacgcc      3240
acatccgaat ggatccaggg caagtacctg cgccgcatcc cggtcacgcc tcaagggatc      3300
gagctaacat ggggaaacaa cgcgccgatg cacttttggt catccgtcag gtacgcatcc      3360
ggggacgctg atgcgtaccc ctgggaactt ctggtgtacc acaccaagca ccatccagag      3420
tacgcgtggg cgtttgtagg agttgcatgc ggcctgctgg ctatcgcagc gtgcatgttt      3480
gcgtgcgcat gcagcagggt gcggtactct ctggtcgcca acacgttcaa ctcgaaccca      3540
ccaccattga ccgcactgac tgcagcactg tgttgcatac caggggctcg cgcggaccaa      3600
ccctacttgg acatcattgc ctacttttta ggggtaagag ggtggtcagc cctgctggtc      3660
atccttgcgt atgtacagag ctgcaagagc tacgaacaca ccgtggtggt cccaatggat      3720
ccaagagccc cgtcgtacga agcagtgata aaccggaatg ggtatgatcc attgaagctg      3780
```

-continued

```
accatctcag tgaatttcac cgtcatctca ccaactacgg ctctggaata ttggacctgc   3840
gcaggagtcc ccatcgtcga gccgccccat gtgggctgct gcacgtcggt gtcctgcccc   3900
tctgacctct ctacgctgca tgcgtttact ggcaaagctg tctccgacgt gcactgcgat   3960
gtgcacacaa acgtgtaccc cttgttgtgg ggcgcggctc actgcttctg ttccaccgag   4020
aatacacagg tcagcgctgt ggcagccacc gtttctgagt tctgtgccca ggactcagag   4080
cgtgccgaag cgttcagcgt acacagcagc tcagtcaccg ctgaggtcct ggtgacgctt   4140
ggtgaagtgg tgacggcagt ccacgtttac gtggacgggg taacatcagc caggggcact   4200
gacctcaaga tcgtggctgg accaataaca accgactact ccccattcga tcgcaaagta   4260
gtccgcatcg gcgaagaggt ctataactat gactggcctc cttacggggc tggccgacca   4320
ggcacattcg gagacattca agctaggtca accaactatg tcaaacccaa cgatctgtat   4380
ggggacatcg gaattgaagt actgcagccg actaacgacc acgtacatgt ggcttacacg   4440
tatacgacct ctgggttact gcgttggctg caggacgctc cgaaaccact cagtgtcaca   4500
gcaccgcacg gttgtaagat cagtgccaat ccgctcctgg ccctcgattg tggggttggt   4560
gccgtcccca tgtccatcaa cattccggac gcgaagttta cccgcaaatt aaaggatccg   4620
aaaccatcgg ccctgaaatg cgtggtggac agctgcgagt acggggtgga ctacgggggc   4680
gccgccacga tcacctacga gggccacgag gccgggaagt gcgggattca ttccctgaca   4740
ccaggagtcc ccctgagaac atcggtggtt gaagtggttg ctggcgccaa taccgtcaaa   4800
acgaccttct cctcacccac gcccgaggtt gcactcgagg tagagatctg ttcggcaata   4860
gtgaagtgcg ctggtgagtg cactccaccg aaggaacatg tggtcgcaac caggcctcgc   4920
catggcagcg accctggagg ctacatctcc gggcccgcaa tgcgctgggc cggagggatt   4980
gtagggaccc tagtggtcct gttccttatc cttgccgtca tctactgcgt ggtgaagaag   5040
tgccgctcca aaagaatccg gatagtcaag agctaaattc cggtatacaa attgctcact   5100
aggagcccat ccgatcccac agggagtagg atgagtcatc tattggtttt aaaattttca   5160
atacaaaaaa aaaaaaaaa                                                5179

<210> SEQ ID NO 2
<211> LENGTH: 394
<212> TYPE: PRT
<213> ORGANISM: Salmon pancreatic disease virus
<220> FEATURE:
<223> OTHER INFORMATION: NSP4 (C-terminal region)

<400> SEQUENCE: 2

Thr Met Asp Ser Ala Ala Met Asn Val Glu Ala Phe Lys Ser Phe Ala
  1               5                  10                  15

Cys Lys Asp Thr Asp Leu Trp Thr Glu Phe Ala Glu Lys Pro Val Arg
             20                  25                  30

Leu Ser Pro Gly Gln Ile Glu Glu Tyr Val Phe His Leu Gln Gly Ala
         35                  40                  45

Lys Ala Asn Val Met His Ser Arg Val Glu Ala Val Cys Pro Asp Leu
     50                  55                  60

Ser Glu Val Ala Met Asp Arg Phe Thr Leu Asp Met Lys Arg Asp Val
 65                  70                  75                  80

Lys Val Thr Pro Gly Thr Lys His Val Glu Glu Arg Pro Lys Val Gln
                 85                  90                  95

Glu Ile Gln Ala Ala Asp Pro Met Ala Thr Ala Tyr Leu Cys Ala Ile
            100                 105                 110
```

```
His Arg Glu Leu Val Arg Arg Leu Lys Ala Val Leu Lys Pro Ser Ile
        115                 120                 125

His Val Leu Phe Asp Met Ser Ser Glu Asp Phe Asp Ala Ile Val Gly
        130                 135                 140

His Gly Met Lys Leu Gly Asp Lys Val Leu Glu Thr Asp Ile Ser Ser
145                 150                 155                 160

Phe Asp Lys Ser Gln Asp Gln Ala Met Ala Val Thr Ala Leu Met Leu
                165                 170                 175

Leu Arg Asp Leu Gly Val Glu Glu Asp Leu Leu Thr Leu Ile Glu Ala
            180                 185                 190

Ser Phe Gly Asp Ile Thr Ser Ala His Leu Pro Thr Gly Thr Arg Phe
        195                 200                 205

Gln Phe Gly Ser Met Met Lys Ser Gly Leu Phe Leu Thr Leu Phe Val
        210                 215                 220

Asn Thr Leu Leu Asn Ile Thr Ile Ala Ala Arg Val Leu Arg Glu Gln
225                 230                 235                 240

Leu Ala Asp Thr Arg Cys Ala Ala Phe Ile Gly Asp Asp Asn Val Ile
                245                 250                 255

Thr Gly Val Val Ser Asp Asp Met Met Val Ala Arg Cys Ala Ser Trp
            260                 265                 270

Leu Asn Met Glu Val Lys Ile Met Asp Met Glu Ile Gly Asn Met Ser
        275                 280                 285

Pro Tyr Phe Cys Gly Gly Phe Leu Leu Leu Asp Thr Val Thr Gly Thr
        290                 295                 300

Val Ser Arg Val Ser Asp Pro Val Lys Arg Leu Met Lys Met Gly Lys
305                 310                 315                 320

Pro Ala Leu Asn Asp Pro Glu Thr Asp Val Asp Arg Cys Arg Ala Leu
                325                 330                 335

Arg Glu Glu Val Glu Ser Trp Tyr Arg Val Gly Ile Gln Trp Pro Leu
            340                 345                 350

Gln Val Ala Ala Ala Thr Arg Tyr Gly Val Asn His Leu Pro Leu Ala
        355                 360                 365

Thr Met Ala Met Ala Thr Leu Ala Gln Asp Leu Arg Ser Tyr Leu Gly
        370                 375                 380

Ala Arg Gly Glu Tyr Val Ser Leu Tyr Val
385                 390

<210> SEQ ID NO 3
<211> LENGTH: 1359
<212> TYPE: PRT
<213> ORGANISM: Salmon pancreatic disease virus
<220> FEATURE:
<223> OTHER INFORMATION: p130

<400> SEQUENCE: 3

Met Pro Arg Thr Ala Arg Arg Ser Gly Lys Leu Val Gln Ser Gly Asp
 1               5                  10                  15

Ser Val Ala Thr Ala Gly Gly Cys Arg His Thr Leu Trp Arg Glu Pro
                20                  25                  30

Pro Ala Ala Gly His Asn Gly Asp Gly His Ala Arg Pro Gly Leu Glu
            35                  40                  45

Ile Val Pro Gly Arg Ala Arg Gly Val Arg Ile Pro Leu Arg Leu Thr
        50                  55                  60

Leu Ile Phe Ser Ala Ser Tyr Phe Gln Thr Ile Met Phe Pro Met Gln
65                  70                  75                  80
```

-continued

```
Phe Thr Asn Ser Ala Tyr Arg Gln Met Glu Pro Met Phe Ala Pro Gly
                 85                  90                  95

Ser Arg Gly Gln Val Gln Pro Tyr Arg Pro Arg Thr Lys Arg Arg Gln
            100                 105                 110

Glu Pro Gln Val Gly Asn Ala Ala Ile Thr Ala Leu Ala Asn Gln Met
            115                 120                 125

Ser Ala Leu Gln Leu Gln Val Ala Gly Leu Ala Gly Gln Ala Arg Val
130                 135                 140

Asp Arg Arg Gly Pro Arg Arg Val Gln Lys Asn Lys Gln Lys Lys Lys
145                 150                 155                 160

Asn Ser Ser Asn Gly Glu Lys Pro Lys Glu Lys Lys Lys Lys Gln Lys
                165                 170                 175

Gln Gln Glu Lys Lys Gly Ser Gly Glu Lys Val Lys Lys Thr Arg
            180                 185                 190

Asn Arg Pro Gly Lys Glu Val Arg Ile Ser Val Lys Cys Ala Arg Gln
            195                 200                 205

Ser Thr Phe Pro Val Tyr His Glu Gly Ala Ile Ser Gly Tyr Ala Val
    210                 215                 220

Leu Ile Gly Ser Arg Val Phe Lys Pro Ala His Val Lys Gly Lys Ile
225                 230                 235                 240

Asp His Pro Glu Leu Ala Asp Ile Lys Phe Gln Val Ala Glu Asp Met
                245                 250                 255

Asp Leu Glu Ala Ala Ala Tyr Pro Lys Ser Met Arg Asp Gln Ala Ala
            260                 265                 270

Glu Pro Ala Thr Met Met Asp Arg Val Tyr Asn Trp Glu Tyr Gly Thr
            275                 280                 285

Ile Arg Val Glu Asp Asn Val Ile Ile Asp Ala Ser Gly Arg Gly Lys
    290                 295                 300

Pro Gly Asp Ser Gly Arg Ala Ile Thr Asp Asn Ser Gly Lys Val Val
305                 310                 315                 320

Gly Ile Val Leu Gly Gly Pro Asp Gly Arg Arg Thr Arg Leu Ser
                325                 330                 335

Val Ile Gly Phe Asp Lys Lys Met Lys Ala Arg Glu Ile Ala Tyr Ser
            340                 345                 350

Asp Ala Ile Pro Trp Thr Arg Ala Pro Ala Leu Leu Leu Leu Pro Met
    355                 360                 365

Val Ile Val Cys Thr Tyr Asn Ser Asn Thr Phe Asp Cys Ser Lys Pro
370                 375                 380

Ser Cys Gln Asp Cys Cys Ile Thr Ala Glu Pro Glu Lys Ala Met Thr
385                 390                 395                 400

Met Leu Lys Asp Asn Leu Asn Asp Pro Asn Tyr Trp Asp Leu Leu Ile
                405                 410                 415

Ala Val Thr Thr Cys Gly Ser Ala Arg Arg Lys Arg Ala Val Ser Thr
            420                 425                 430

Ser Pro Ala Ala Phe Tyr Asp Thr Gln Ile Leu Ala Ala His Ala Ala
            435                 440                 445

Ala Ser Pro Tyr Arg Ala Tyr Cys Pro Asp Cys Asp Gly Thr Ala Cys
    450                 455                 460

Ile Ser Pro Ile Ala Ile Asp Glu Val Val Ser Ser Gly Ser Asp His
465                 470                 475                 480

Val Leu Arg Met Arg Val Gly Ser Gln Ser Gly Val Thr Ala Lys Gly
                485                 490                 495
```

-continued

```
Gly Ala Ala Gly Glu Thr Ser Leu Arg Tyr Leu Gly Arg Asp Gly Lys
            500                 505                 510

Val His Ala Ala Asp Asn Thr Arg Leu Val Val Arg Thr Thr Ala Lys
            515                 520                 525

Cys Asp Val Leu Gln Ala Thr Gly His Tyr Ile Leu Ala Asn Cys Pro
            530                 535                 540

Val Gly Gln Ser Leu Thr Val Ala Ala Thr Leu Asp Gly Thr Arg His
545                 550                 555                 560

Gln Cys Thr Thr Val Phe Glu His Gln Val Thr Glu Lys Phe Thr Arg
                565                 570                 575

Glu Arg Ser Lys Gly His His Leu Ser Asp Met Thr Lys Lys Cys Thr
            580                 585                 590

Arg Phe Ser Thr Thr Pro Lys Lys Ser Ala Leu Tyr Leu Val Asp Val
            595                 600                 605

Tyr Asp Ala Leu Pro Ile Ser Val Glu Ile Ser Thr Val Val Thr Cys
            610                 615                 620

Ser Asp Ser Gln Cys Thr Val Arg Val Pro Pro Gly Thr Thr Val Lys
625                 630                 635                 640

Phe Asp Lys Lys Cys Lys Ser Ala Asp Ser Ala Thr Val Thr Phe Thr
                645                 650                 655

Ser Asp Ser Gln Thr Phe Thr Cys Glu Glu Pro Val Leu Thr Ala Ala
            660                 665                 670

Ser Ile Thr Gln Gly Lys Pro His Leu Arg Ser Ala Met Leu Pro Ser
            675                 680                 685

Gly Gly Lys Glu Val Lys Ala Arg Ile Pro Phe Pro Phe Pro Pro Glu
            690                 695                 700

Thr Ala Thr Cys Arg Val Ser Val Ala Pro Leu Pro Ser Ile Thr Tyr
705                 710                 715                 720

Glu Glu Ser Asp Val Leu Leu Ala Gly Thr Ala Lys Tyr Pro Val Leu
                725                 730                 735

Leu Thr Thr Arg Asn Leu Gly Phe His Ser Asn Ala Thr Ser Glu Trp
            740                 745                 750

Ile Gln Gly Lys Tyr Leu Arg Arg Ile Pro Val Thr Pro Gln Gly Ile
            755                 760                 765

Glu Leu Thr Trp Gly Asn Asn Ala Pro Met His Phe Trp Ser Ser Val
            770                 775                 780

Arg Tyr Ala Ser Gly Asp Ala Asp Ala Tyr Pro Trp Glu Leu Leu Val
785                 790                 795                 800

Tyr His Thr Lys His His Pro Glu Tyr Ala Trp Ala Phe Val Gly Val
                805                 810                 815

Ala Cys Gly Leu Leu Ala Ile Ala Ala Cys Met Phe Ala Cys Ala Cys
            820                 825                 830

Ser Arg Val Arg Tyr Ser Leu Val Ala Asn Thr Phe Asn Ser Asn Pro
            835                 840                 845

Pro Pro Leu Thr Ala Leu Thr Ala Ala Leu Cys Cys Ile Pro Gly Ala
            850                 855                 860

Arg Ala Asp Gln Pro Tyr Leu Asp Ile Ile Ala Tyr Phe Leu Gly Val
865                 870                 875                 880

Arg Gly Trp Ser Ala Leu Leu Val Ile Leu Ala Tyr Val Gln Ser Cys
                885                 890                 895

Lys Ser Tyr Glu His Thr Val Val Val Pro Met Asp Pro Arg Ala Pro
            900                 905                 910
```

```
Ser Tyr Glu Ala Val Ile Asn Arg Asn Gly Tyr Asp Pro Leu Lys Leu
        915                 920                 925

Thr Ile Ser Val Asn Phe Thr Val Ile Ser Pro Thr Thr Ala Leu Glu
        930                 935                 940

Tyr Trp Thr Cys Ala Gly Val Pro Ile Val Glu Pro Pro His Val Gly
945                 950                 955                 960

Cys Cys Thr Ser Val Ser Cys Pro Ser Asp Leu Ser Thr Leu His Ala
            965                 970                 975

Phe Thr Gly Lys Ala Val Ser Asp Val His Cys Asp Val His Thr Asn
            980                 985                 990

Val Tyr Pro Leu Leu Trp Gly Ala His Cys Phe Cys Ser Thr Glu
        995                 1000                1005

Asn Thr Gln Val Ser Ala Val Ala Ala Thr Val Ser Glu Phe Cys Ala
        1010                1015                1020

Gln Asp Ser Glu Arg Ala Glu Ala Phe Ser Val His Ser Ser Ser Val
1025                1030                1035                1040

Thr Ala Glu Val Leu Val Thr Leu Gly Glu Val Val Thr Ala Val His
                1045                1050                1055

Val Tyr Val Asp Gly Val Thr Ser Ala Arg Gly Thr Asp Leu Lys Ile
                1060                1065                1070

Val Ala Gly Pro Ile Thr Thr Asp Tyr Ser Pro Phe Asp Arg Lys Val
                1075                1080                1085

Val Arg Ile Gly Glu Glu Val Tyr Asn Tyr Asp Trp Pro Pro Tyr Gly
                1090                1095                1100

Ala Gly Arg Pro Gly Thr Phe Gly Asp Ile Gln Ala Arg Ser Thr Asn
1105                1110                1115                1120

Tyr Val Lys Pro Asn Asp Leu Tyr Gly Asp Ile Gly Ile Glu Val Leu
                1125                1130                1135

Gln Pro Thr Asn Asp His Val His Val Ala Tyr Thr Tyr Thr Thr Ser
                1140                1145                1150

Gly Leu Leu Arg Trp Leu Gln Asp Ala Pro Lys Pro Leu Ser Val Thr
                1155                1160                1165

Ala Pro His Gly Cys Lys Ile Ser Ala Asn Pro Leu Leu Ala Leu Asp
                1170                1175                1180

Cys Gly Val Gly Ala Val Pro Met Ser Ile Asn Ile Pro Asp Ala Lys
1185                1190                1195                1200

Phe Thr Arg Lys Leu Lys Asp Pro Lys Pro Ser Ala Leu Lys Cys Val
                1205                1210                1215

Val Asp Ser Cys Glu Tyr Gly Val Asp Tyr Gly Gly Ala Ala Thr Ile
                1220                1225                1230

Thr Tyr Glu Gly His Glu Ala Gly Lys Cys Gly Ile His Ser Leu Thr
                1235                1240                1245

Pro Gly Val Pro Leu Arg Thr Ser Val Glu Val Val Ala Gly Ala
                1250                1255                1260

Asn Thr Val Lys Thr Thr Phe Ser Ser Pro Thr Pro Glu Val Ala Leu
1265                1270                1275                1280

Glu Val Glu Ile Cys Ser Ala Ile Val Lys Cys Ala Gly Glu Cys Thr
                1285                1290                1295

Pro Pro Lys Glu His Val Val Ala Thr Arg Pro Arg His Gly Ser Asp
                1300                1305                1310

Pro Gly Gly Tyr Ile Ser Gly Pro Ala Met Arg Trp Ala Gly Gly Ile
                1315                1320                1325
```

```
Val Gly Thr Leu Val Val Leu Phe Leu Ile Leu Ala Val Ile Tyr Cys
    1330                1335                1340

Val Val Lys Lys Cys Arg Ser Lys Arg Ile Arg Ile Val Lys Ser
1345                1350                1355

<210> SEQ ID NO 4
<211> LENGTH: 282
<212> TYPE: PRT
<213> ORGANISM: Salmon pancreatic disease virus
<220> FEATURE:
<223> OTHER INFORMATION: capsid

<400> SEQUENCE: 4

Met Phe Pro Met Gln Phe Thr Asn Ser Ala Tyr Arg Gln Met Glu Pro
  1               5                  10                  15

Met Phe Ala Pro Gly Ser Arg Gly Gln Val Gln Pro Tyr Arg Pro Arg
             20                  25                  30

Thr Lys Arg Arg Gln Glu Pro Gln Val Gly Asn Ala Ala Ile Thr Ala
         35                  40                  45

Leu Ala Asn Gln Met Ser Ala Leu Gln Leu Gln Val Ala Gly Leu Ala
     50                  55                  60

Gly Gln Ala Arg Val Asp Arg Arg Gly Pro Arg Arg Val Gln Lys Asn
 65                  70                  75                  80

Lys Gln Lys Lys Lys Asn Ser Ser Asn Gly Glu Lys Pro Lys Glu Lys
                 85                  90                  95

Lys Lys Lys Gln Lys Gln Gln Glu Lys Lys Gly Ser Gly Gly Glu Lys
            100                 105                 110

Val Lys Lys Thr Arg Asn Arg Pro Gly Lys Glu Val Arg Ile Ser Val
        115                 120                 125

Lys Cys Ala Arg Gln Ser Thr Phe Pro Val Tyr His Glu Gly Ala Ile
    130                 135                 140

Ser Gly Tyr Ala Val Leu Ile Gly Ser Arg Val Phe Lys Pro Ala His
145                 150                 155                 160

Val Lys Gly Lys Ile Asp His Pro Glu Leu Ala Asp Ile Lys Phe Gln
                165                 170                 175

Val Ala Glu Asp Met Asp Leu Glu Ala Ala Tyr Pro Lys Ser Met
            180                 185                 190

Arg Asp Gln Ala Ala Glu Pro Ala Thr Met Met Asp Arg Val Tyr Asn
        195                 200                 205

Trp Glu Tyr Gly Thr Ile Arg Val Glu Asp Asn Val Ile Ile Asp Ala
    210                 215                 220

Ser Gly Arg Gly Lys Pro Gly Asp Ser Gly Arg Ala Ile Thr Asp Asn
225                 230                 235                 240

Ser Gly Lys Val Val Gly Ile Val Leu Gly Gly Pro Asp Gly Arg
                245                 250                 255

Arg Thr Arg Leu Ser Val Ile Gly Phe Asp Lys Lys Met Lys Ala Arg
            260                 265                 270

Glu Ile Ala Tyr Ser Asp Ala Ile Pro Trp
        275                 280

<210> SEQ ID NO 5
<211> LENGTH: 71
<212> TYPE: PRT
<213> ORGANISM: Salmon pancreatic disease virus
<220> FEATURE:
<223> OTHER INFORMATION: E3
```

```
<400> SEQUENCE: 5

Thr Arg Ala Pro Ala Leu Leu Leu Pro Met Val Ile Val Cys Thr
 1               5                  10                  15

Tyr Asn Ser Asn Thr Phe Asp Cys Ser Lys Pro Ser Cys Gln Asp Cys
                20                  25                  30

Cys Ile Thr Ala Glu Pro Glu Lys Ala Met Thr Met Leu Lys Asp Asn
            35                  40                  45

Leu Asn Asp Pro Asn Tyr Trp Asp Leu Leu Ile Ala Val Thr Thr Cys
        50                  55                  60

Gly Ser Ala Arg Arg Lys Arg
 65                  70

<210> SEQ ID NO 6
<211> LENGTH: 438
<212> TYPE: PRT
<213> ORGANISM: Salmon pancreatic disease virus
<220> FEATURE:
<223> OTHER INFORMATION: E2

<400> SEQUENCE: 6

Ala Val Ser Thr Ser Pro Ala Ala Phe Tyr Asp Thr Gln Ile Leu Ala
 1               5                  10                  15

Ala His Ala Ala Ala Ser Pro Tyr Arg Ala Tyr Cys Pro Asp Cys Asp
                20                  25                  30

Gly Thr Ala Cys Ile Ser Pro Ile Ala Ile Asp Glu Val Val Ser Ser
            35                  40                  45

Gly Ser Asp His Val Leu Arg Met Arg Val Gly Ser Gln Ser Gly Val
        50                  55                  60

Thr Ala Lys Gly Gly Ala Ala Gly Glu Thr Ser Leu Arg Tyr Leu Gly
 65                  70                  75                  80

Arg Asp Gly Lys Val His Ala Ala Asp Asn Thr Arg Leu Val Val Arg
                85                  90                  95

Thr Thr Ala Lys Cys Asp Val Leu Gln Ala Thr Gly His Tyr Ile Leu
            100                 105                 110

Ala Asn Cys Pro Val Gly Gln Ser Leu Thr Val Ala Ala Thr Leu Asp
        115                 120                 125

Gly Thr Arg His Gln Cys Thr Thr Val Phe Glu His Gln Val Thr Glu
130                 135                 140

Lys Phe Thr Arg Glu Arg Ser Lys Gly His His Leu Ser Asp Met Thr
145                 150                 155                 160

Lys Lys Cys Thr Arg Phe Ser Thr Thr Pro Lys Lys Ser Ala Leu Tyr
                165                 170                 175

Leu Val Asp Val Tyr Asp Ala Leu Pro Ile Ser Val Glu Ile Ser Thr
            180                 185                 190

Val Val Thr Cys Ser Asp Ser Gln Cys Thr Val Arg Val Pro Pro Gly
        195                 200                 205

Thr Thr Val Lys Phe Asp Lys Lys Cys Lys Ser Ala Asp Ser Ala Thr
210                 215                 220

Val Thr Phe Thr Ser Asp Ser Gln Thr Phe Thr Cys Glu Glu Pro Val
225                 230                 235                 240

Leu Thr Ala Ala Ser Ile Thr Gln Gly Lys Pro His Leu Arg Ser Ala
                245                 250                 255

Met Leu Pro Ser Gly Gly Lys Glu Val Lys Ala Arg Ile Pro Phe Pro
            260                 265                 270
```

-continued

```
Phe Pro Pro Glu Thr Ala Thr Cys Arg Val Ser Val Ala Pro Leu Pro
        275                 280                 285

Ser Ile Thr Tyr Glu Glu Ser Asp Val Leu Leu Ala Gly Thr Ala Lys
    290                 295                 300

Tyr Pro Val Leu Leu Thr Thr Arg Asn Leu Gly Phe His Ser Asn Ala
305                 310                 315                 320

Thr Ser Glu Trp Ile Gln Gly Lys Tyr Leu Arg Arg Ile Pro Val Thr
                325                 330                 335

Pro Gln Gly Ile Glu Leu Thr Trp Gly Asn Asn Ala Pro Met His Phe
            340                 345                 350

Trp Ser Ser Val Arg Tyr Ala Ser Gly Asp Ala Asp Ala Tyr Pro Trp
        355                 360                 365

Glu Leu Leu Val Tyr His Thr Lys His His Pro Glu Tyr Ala Trp Ala
    370                 375                 380

Phe Val Gly Val Ala Cys Gly Leu Leu Ala Ile Ala Ala Cys Met Phe
385                 390                 395                 400

Ala Cys Ala Cys Ser Arg Val Arg Tyr Ser Leu Val Ala Asn Thr Phe
                405                 410                 415

Asn Ser Asn Pro Pro Pro Leu Thr Ala Leu Thr Ala Ala Leu Cys Cys
            420                 425                 430

Ile Pro Gly Ala Arg Ala
        435

<210> SEQ ID NO 7
<211> LENGTH: 32
<212> TYPE: PRT
<213> ORGANISM: Salmon pancreatic disease virus
<220> FEATURE:
<223> OTHER INFORMATION: 6K

<400> SEQUENCE: 7

Asp Gln Pro Tyr Leu Asp Ile Ile Ala Tyr Phe Leu Gly Val Arg Gly
  1               5                  10                  15

Trp Ser Ala Leu Leu Val Ile Leu Ala Tyr Val Gln Ser Cys Lys Ser
             20                  25                  30

<210> SEQ ID NO 8
<211> LENGTH: 461
<212> TYPE: PRT
<213> ORGANISM: Salmon pancreatic disease virus
<220> FEATURE:
<223> OTHER INFORMATION: E1

<400> SEQUENCE: 8

Tyr Glu His Thr Val Val Val Pro Met Asp Pro Arg Ala Pro Ser Tyr
  1               5                  10                  15

Glu Ala Val Ile Asn Arg Asn Gly Tyr Asp Pro Leu Lys Leu Thr Ile
             20                  25                  30

Ser Val Asn Phe Thr Val Ile Ser Pro Thr Thr Ala Leu Glu Tyr Trp
         35                  40                  45

Thr Cys Ala Gly Val Pro Ile Val Glu Pro Pro His Val Gly Cys Cys
     50                  55                  60

Thr Ser Val Ser Cys Pro Ser Asp Leu Ser Thr Leu His Ala Phe Thr
 65                  70                  75                  80

Gly Lys Ala Val Ser Asp Val His Cys Asp Val His Thr Asn Val Tyr
                 85                  90                  95

Pro Leu Leu Trp Gly Ala Ala His Cys Phe Cys Ser Thr Glu Asn Thr
            100                 105                 110
```

```
Gln Val Ser Ala Val Ala Ala Thr Val Ser Glu Phe Cys Ala Gln Asp
        115                 120                 125

Ser Glu Arg Ala Glu Ala Phe Ser Val His Ser Ser Val Thr Ala
130                 135                 140

Glu Val Leu Val Thr Leu Gly Glu Val Val Thr Ala Val His Val Tyr
145                 150                 155                 160

Val Asp Gly Val Thr Ser Ala Arg Gly Thr Asp Leu Lys Ile Val Ala
                165                 170                 175

Gly Pro Ile Thr Thr Asp Tyr Ser Pro Phe Asp Arg Lys Val Val Arg
            180                 185                 190

Ile Gly Glu Glu Val Tyr Asn Tyr Asp Trp Pro Pro Tyr Gly Ala Gly
        195                 200                 205

Arg Pro Gly Thr Phe Gly Asp Ile Gln Ala Arg Ser Thr Asn Tyr Val
    210                 215                 220

Lys Pro Asn Asp Leu Tyr Gly Asp Ile Gly Ile Glu Val Leu Gln Pro
225                 230                 235                 240

Thr Asn Asp His Val His Val Ala Tyr Thr Tyr Thr Thr Ser Gly Leu
                245                 250                 255

Leu Arg Trp Leu Gln Asp Ala Pro Lys Pro Leu Ser Val Thr Ala Pro
            260                 265                 270

His Gly Cys Lys Ile Ser Ala Asn Pro Leu Leu Ala Leu Asp Cys Gly
        275                 280                 285

Val Gly Ala Val Pro Met Ser Ile Asn Ile Pro Asp Ala Lys Phe Thr
    290                 295                 300

Arg Lys Leu Lys Asp Pro Lys Pro Ser Ala Leu Lys Cys Val Val Asp
305                 310                 315                 320

Ser Cys Glu Tyr Gly Val Asp Tyr Gly Gly Ala Ala Thr Ile Thr Tyr
                325                 330                 335

Glu Gly His Glu Ala Gly Lys Cys Gly Ile His Ser Leu Thr Pro Gly
            340                 345                 350

Val Pro Leu Arg Thr Ser Val Val Glu Val Val Ala Gly Ala Asn Thr
        355                 360                 365

Val Lys Thr Thr Phe Ser Ser Pro Thr Pro Glu Val Ala Leu Glu Val
    370                 375                 380

Glu Ile Cys Ser Ala Ile Val Lys Cys Ala Gly Glu Cys Thr Pro Pro
385                 390                 395                 400

Lys Glu His Val Val Ala Thr Arg Pro Arg His Gly Ser Asp Pro Gly
                405                 410                 415

Gly Tyr Ile Ser Gly Pro Ala Met Arg Trp Ala Gly Gly Ile Val Gly
            420                 425                 430

Thr Leu Val Val Leu Phe Leu Ile Leu Ala Val Ile Tyr Cys Val Val
        435                 440                 445

Lys Lys Cys Arg Ser Lys Arg Ile Arg Ile Val Lys Ser
    450                 455                 460

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 9
tgcatgcggc cgcatgtttc ccatgcaatt caccaac                              37
```

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 10
tgcatgcggc cgcttgtatt gaaaatttta aaaccaa                              37

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 11
tgcatgcggc cgcatgacac gcgctccggc cctcctg                              37

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 12
tgcatgcggc cgctcacgcg cgagcccctg gtatgcaaca                           40

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 13
tgcatgcggc cgcatggctg tgtctacgtc gcctgcc                              37

<210> SEQ ID NO 14
<211> LENGTH: 204
<212> TYPE: DNA
<213> ORGANISM: Salmon pancreatic disease virus
<220> FEATURE:
<221> NAME/KEY: CDS
<222> LOCATION: (1)..(204)
<223> OTHER INFORMATION: 6K

<400> SEQUENCE: 14

```
gac caa ccc tac ttg gac atc att gcc tac ttg tgg acc aac agc aaa      48
Asp Gln Pro Tyr Leu Asp Ile Ile Ala Tyr Leu Trp Thr Asn Ser Lys
 1               5                  10                  15 gtg gcc ttc ggg cta caa ttt gcg gcg ccc gtg gcc tgt gtg ctc atc      96
Val Ala Phe Gly Leu Gln Phe Ala Ala Pro Val Ala Cys Val Leu Ile
             20                  25                  30 att aca tac gcc ctt agg cac tgc aga ttg tgc tgc aag tct ttt tta    144
Ile Thr Tyr Ala Leu Arg His Cys Arg Leu Cys Cys Lys Ser Phe Leu
         35                  40                  45 ggg gta aga ggg tgg tca gcc ctg ctg gtc atc ctt gcg tat gta cag    192
Gly Val Arg Gly Trp Ser Ala Leu Leu Val Ile Leu Ala Tyr Val Gln
     50                  55                  60 agc tgc aag agc                                                    204
Ser Cys Lys Ser
 65
```

-continued

```
<210> SEQ ID NO 15
<211> LENGTH: 68
<212> TYPE: PRT
<213> ORGANISM: Salmon pancreatic disease virus

<400> SEQUENCE: 15

Asp Gln Pro Tyr Leu Asp Ile Ile Ala Tyr Leu Trp Thr Asn Ser Lys
  1               5                  10                  15

Val Ala Phe Gly Leu Gln Phe Ala Ala Pro Val Ala Cys Val Leu Ile
             20                  25                  30

Ile Thr Tyr Ala Leu Arg His Cys Arg Leu Cys Cys Lys Ser Phe Leu
         35                  40                  45

Gly Val Arg Gly Trp Ser Ala Leu Leu Val Ile Leu Ala Tyr Val Gln
     50                  55                  60

Ser Cys Lys Ser
 65
```